United States Patent [19]

Blanchard

[11] Patent Number: 4,855,595

[45] Date of Patent: Aug. 8, 1989

[54] ELECTRIC FIELD CONTROL IN ION MOBILITY SPECTROMETRY

[75] Inventor: William C. Blanchard, Baltimore, Md.

[73] Assignee: Allied-Signal Inc., Morristown, N.J.

[21] Appl. No.: 881,871

[22] Filed: Jul. 3, 1986

[51] Int. Cl.[4] ............................................. H01J 49/40
[52] U.S. Cl. .................................. 250/287; 250/282; 250/286; 250/281
[58] Field of Search ............... 250/281, 282, 286, 287, 250/290

[56] References Cited

U.S. PATENT DOCUMENTS

| | | | |
|---|---|---|---|
| 3,226,543 | 12/1965 | Melzner | 250/287 |
| 3,258,592 | 6/1966 | Blauth et al. | 250/286 |
| 3,593,018 | 7/1971 | Cohen | 250/287 |
| 3,626,182 | 12/1971 | Cohen | 250/287 |
| 4,072,862 | 2/1978 | Mamyrin et al. | 250/287 |
| 4,378,499 | 3/1983 | Spangler et al. | 250/287 |
| 4,390,784 | 6/1983 | Browning et al. | 250/287 |
| 4,458,149 | 7/1984 | Muga | 250/287 |

Primary Examiner—Bruce C. Anderson
Assistant Examiner—Paul A. Guss
Attorney, Agent, or Firm—Robert M. Trepp; Bruce L. Lamb

[57] ABSTRACT

An ion mobility spectrometer for detecting ions and for facilitating controlled chemical reactions is described incorporating an inlet for carrier and sample gas, a reaction region having an ionization source and at least two electrodes for generating an electric field and a drift region having at least two electrodes for generating an electric field therein wherein each electrode is coupled to a power supply for placing a predetermined potential on the electrode and wherein each power supply is controlled by an electric field controller for providing a sequence of potentials on each electrode in the reaction region and drift region to control the motion and position of ions in the drift region. The invention overcomes the problem of detection sensitivity, detection selectivity and resolution between ions of similar mobility. The invention further overcomes the problem of facilitating certain chemical reactions by brings ions of opposite polarity together.

24 Claims, 14 Drawing Sheets

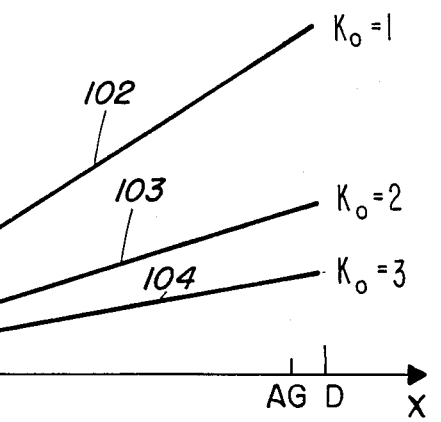

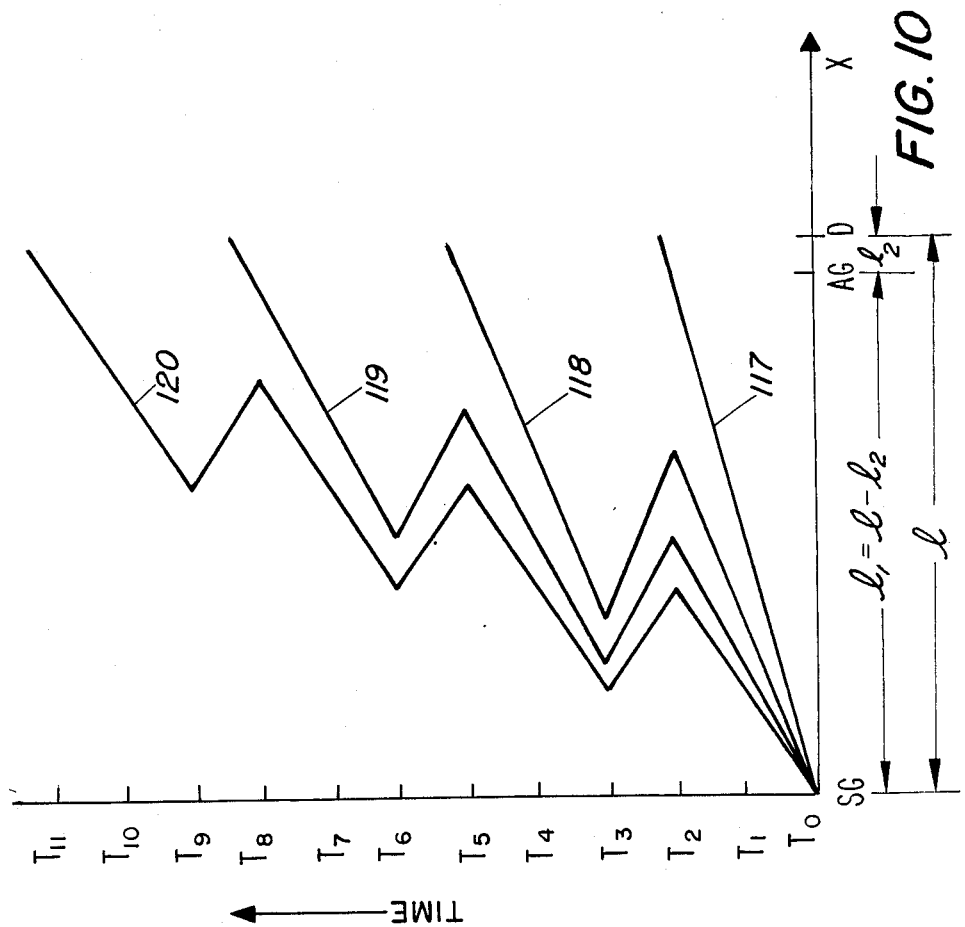
FIG. 10
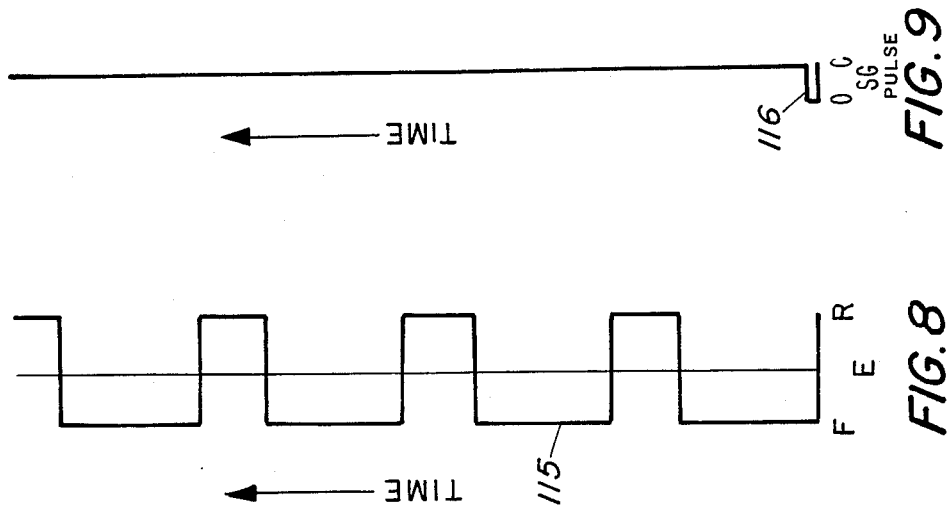
FIG. 9
FIG. 8

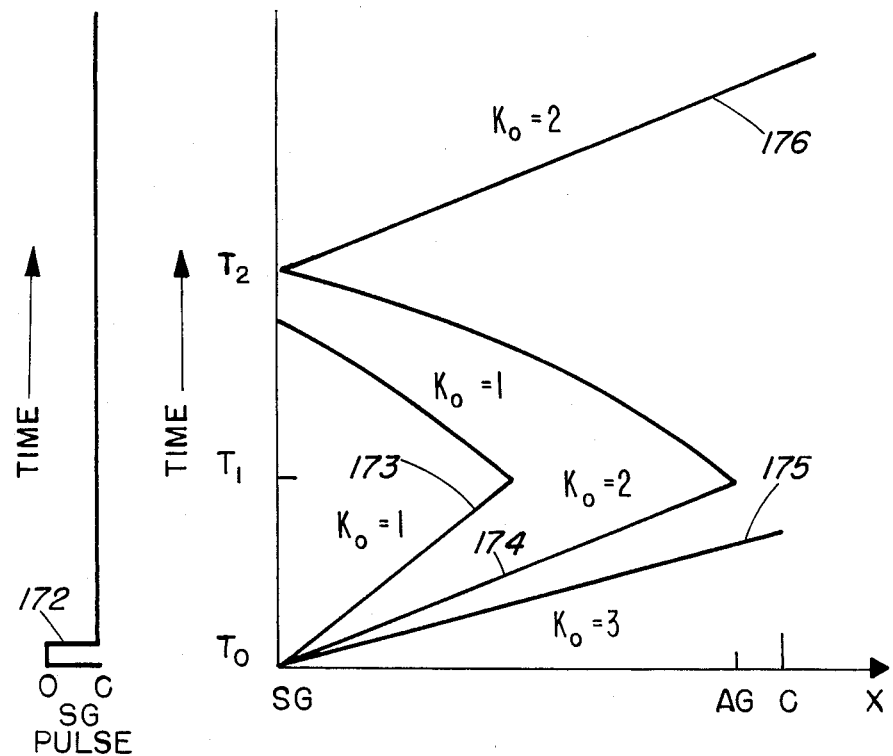
*FIG. 24*     *FIG. 25*
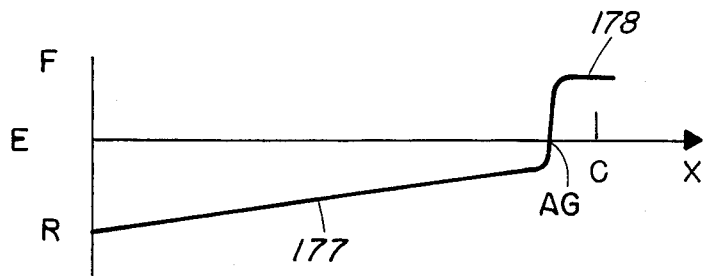
*FIG. 26*

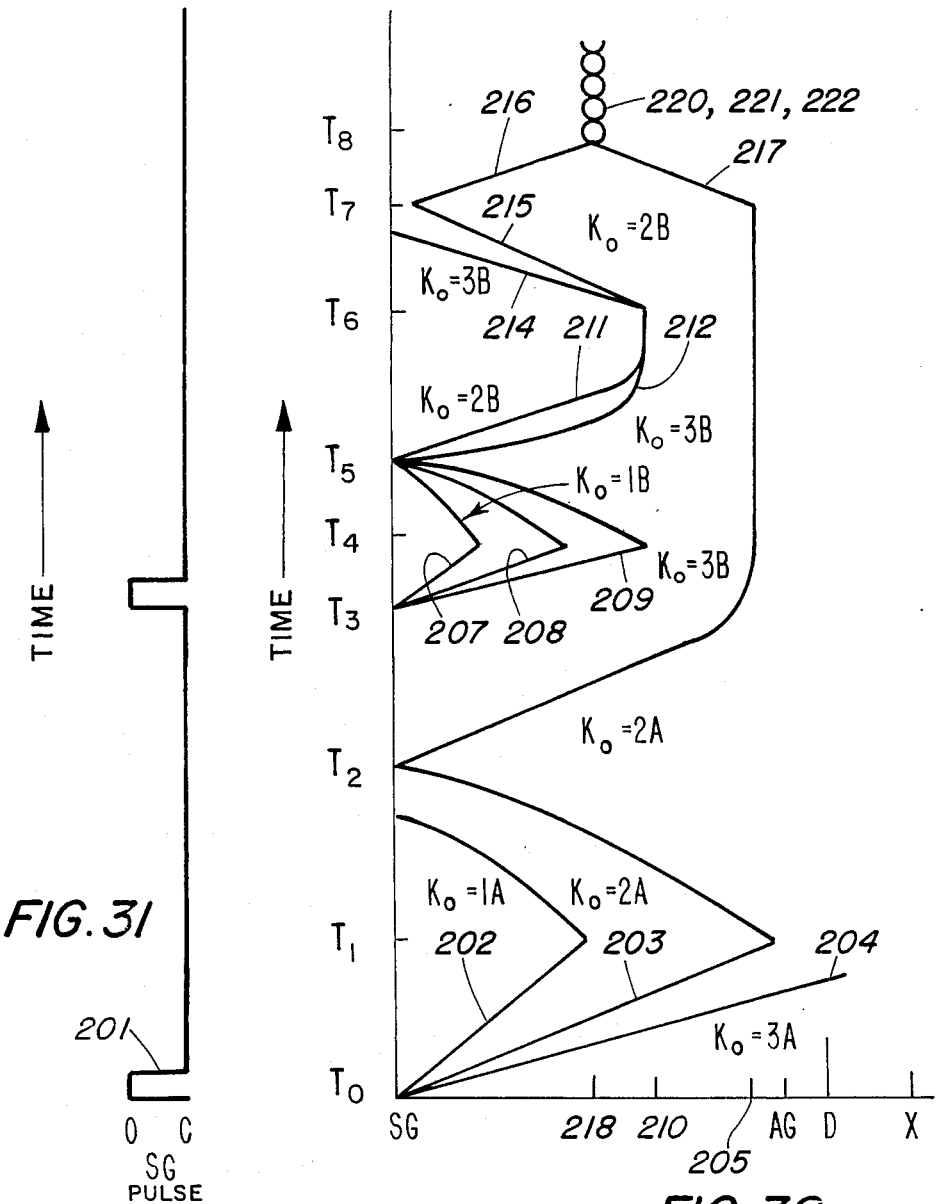
FIG. 31
FIG. 32
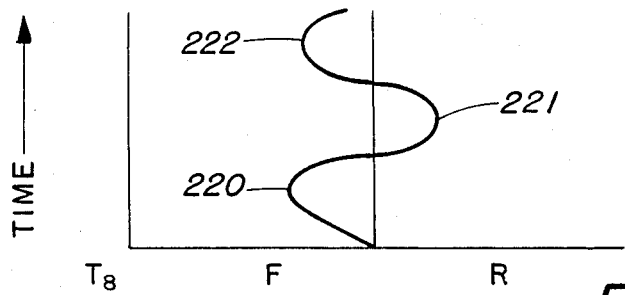
FIG. 33

ELECTRIC FIELD CONTROL IN ION MOBILITY SPECTROMETRY

BACKGROUND OF THE INVENTION

1. Field of the Invention

This invention relates to ion mobility spectrometers and more particularly to controlling selected ions therein by selective sequencing of linear and non-linear electric fields.

2. Description of the Prior Art

The techniques of using ion mobility at atmospheric pressure for spectrometry has been well established. The major parts of an ion mobility spectrometer (IMS) device are: the sample inlet, ionization region, shutter grid, drift region and ion detector. In conventional IMS, a uniform or linear field, for example, 200 V per centimeter, is applied across the drift region and the various ions upon release by the shutter grid are allowed to drift through the drift region toward the ion detector. After release by the shutter grid, the ions of a particular mobility, $K_0$, are located at a particular location in the drift region at each instant of time. The ion detector provides a signal indicative of the number of ions arriving at a collector plate and the time lapse from the time the shutter grid was pulsed open to the time the ions arrive at the collector is an indication of the mobility of the ions collected.

The electric field in the drift region of an ion mobility spectrometer may be provided in two ways. The first way is described in U.S. Pat. No. 4,378,499 which issued on Mar. 29, 1983 to G. E. Spangler, D. N. Campbell and S. Seeb wherein the drift region having a longitudinal axis is surrounded by a plurality of concentric conductive rings 22 separated from one another by a plurality of insulating rings 23 which are secured into a unitary cylindrical body. A voltage divider 24 connected across the output of a high voltage bias source 25 applies progressively increasing voltages to the conductive rings 22 thereby creating the electric field. A second way is shown in U.S. Pat. No. 4,390,784 which issued on June 28, 1983 to D. R. Browning et al. In U.S. Pat. No. 4,390,784 a tube 14a has a thick film resistor 34 coated on its inside surface. A voltage potential difference represented by 36a and derived from high voltage source 36 is impressed across resistor 34 thus causing an electrostatic drift field in drift region 14 which moves ions toward an ion detector. Tube 14a is cylindrical in shape.

SUMMARY OF THE INVENTION

A method and apparatus is described for detecting ions comprising an inlet for introducing a carrier gas and a sample gas into a reaction region, a radioactive source for generating ions from the carrier gas and sample gas in the reaction region, a plurality of rings surrounding the reaction region for generating an electric field in the reaction region to move the ions toward a drift region having a longitudinal axis, a plurality of rings surrounding the drift region for generating an electric field in the drift region substantially parallel to the longitudinal axis, and power supplies and switches for generating a sequence of electric fields in the drift region substantially parallel to the longtitudinal axis to control the position of selected ions in the drift region.

The invention further incudes a sequence of electric fields wherein the electric field is substantially parallel to the longitudinal axis to move ions toward a collector at first times, for reversing the electric field substantially parallel to the longitudinal axis to move ions away from the collector at second times and for generating an electric field in the drift regiin substantially parallel to the longitudinal axis for moving ions toward the collector at third times. The invention further includes adding ions from the reaction region to the first end of the drift region at times selected ions are positioned at that end of the drift region to increase the number of ions in the drift region prior to collecting the ions at a collector at the other end.

The invention further includes generatingg an electric field in the drift region substantially parallel to the longitudinal axis, the electric field of first times having a first direction at the first end to accept ions from the reaction region, and a transition region between the first and second ends where the electric field reverses direction with respect to the first direction to provide an ion well for holding ions, the electric in the drift region at second times having the first direction from the first end to the second end to move the ions toward a collector. Prior to the second times, the magnitude of the electric field in the transition region may be increased to compress the ions within a shorter distance along the longitudinal axis in the transition region.

The invention further provides a method and apparatus for detecting ions comprising, an inlet for introducing the carrier gas and sample gas into a reaction region, a radiation source for generating ions from the carrier gas and sample gas in the reaction region, a plurality of rings surrounding the reaction region for generating an electric field in the reaction region to move the ions toward a first end of a drift region having a second end and a longitudinal axis, a plurality of rings surrounding the drift region for generating an electric field in the drift region substantially parallel to the longitudinal axis wherein the magnitude of the electric field is a function of longitudinal distance from the first end of the drift region. The magnitude of the electric field may, for example, increase or decrease as a function of longitudinal distance from the first end of the drift region to provide separation of ion as a function of mobility.

The invention further provides a method and apparatus for identification of ionized molecules having a similar mobility ($K_0$) but having dissimilar atomic mass unit (AMU) and fracturing energy levels comprising an inlet for introducing a carrier gas and a sample gas into a reaction region, a radioactive source for generating ions from the carrier gas and sample gas in the reaction region, a plurality of rings surrounding the reaction region for generating an electric field in the reaction region to move the ions toward a first end of the drift region having a second end an a longitudinal axis, a plurality of rings surrounding the drift region coupled through a plurality of switches to a plurality of power supplies for generating a sequence of electric fields at predetermined times in the drift region substantially parallel to the longitudinal axis to isolate and position the ionized molecules having a similar mobility in the drift region, fracturing a portion of the ionized molecules, for example, by applying a electric field of predetermined intensity, an arc discharge, or ultraviolet emission, to form daughter ions as a function of fracturing energy, generating a sequence of electric fields at predetermined times in the drift region substantially parallel to the longitudinal axis to reposition and move the ionized molecules and daugher ions toward a collector positioned at the second end of the drift region.

The invention further provides a method and apparatus for chemically reacting selected ions of predetermined mobility comprising an inlet for introducing a carrier gas and one or more sample gasses into a reaction region, a radioactive source for generating positive and negative ions from the carrier gas and the one or more sample gasses in the reaction region, a plurality of rings surrounding the reaction region for generating an electric field in the reaction region to move ions of a first polarity at first times and ions of second polarity at second times toward a first end of a drift region having a second end and a longitudinal axis, a plurality of rings surrounding the drift region coupled through switches to a plurality of power supplies for generating a sequence of electric fields at predetermined times in the drift region substantially parallel to the longitudinal axis to isolate and position ions of the first polarity having a predetermined mobility in the drift region at a first predetermined distance from the first end, and for generating a sequence of electric fields at predetermined times in the drift region at distances less than the first predetermined distance from the first end substantially parallel to the longitudinal axis to isolate and position ions of the second polarity having a predetermined mobility at a second predetermined distance from the first end, and subsequently generating an electric field in the drift region to move the ions of the first polarity and the ions of the second polarity toward each other whereby they chemically combine. A membrane may be positioned transverse to the longitudinal axis in the drift region and between the first and second predetermined distances in the drift region which may be or contain a catalyst to aid a chemical reaction or include a means for maintaining a predetermined temperature of the membrane.

It is an object of the invention to enhance the sensitivity and resolution of commonly used ion mobility spectrometers (IMS) devices.

It is a further object to use electric fields having a constant magnitude and variable magnitude as a function of distance in the drift field wherein the electric fields are static over a predetermined time interval with a timed sequence of electric fields to control the ions so the ions will be positioned in the drift region of an IMS device at a particular location at a particular time.

It is a further object of the invention that by using an electric field having a variable magnitude and polarity as a function of distance (non-linear fields), a selected reduced ion mobility ($K_0$) can be trapped, fractured, and have the resultant daughter ions detected (IMS/IMS).

It is a further object of the invention to provide an electric field sequence in the drift region that negates past history of mobility of the ions by bringing all ions together to substantially a common position on the longitudinal axis.

It is a further object of the invention to simultaneously trap both positive and negative charged ions, to focus ions inward along the longitudinal axis of the drift region, and to sequentially pass ions of incremental $K_0$'s for detection during spaced apart time intervals.

BRIEF DESCRIPTION OF THE DRAWING

FIGS. 2 through 33 show waveforms for various modes of operation of the embodiment of FIG. 1.

DESCRIPTION OF THE PREFERRED EMBODIMENT

Figure 1:
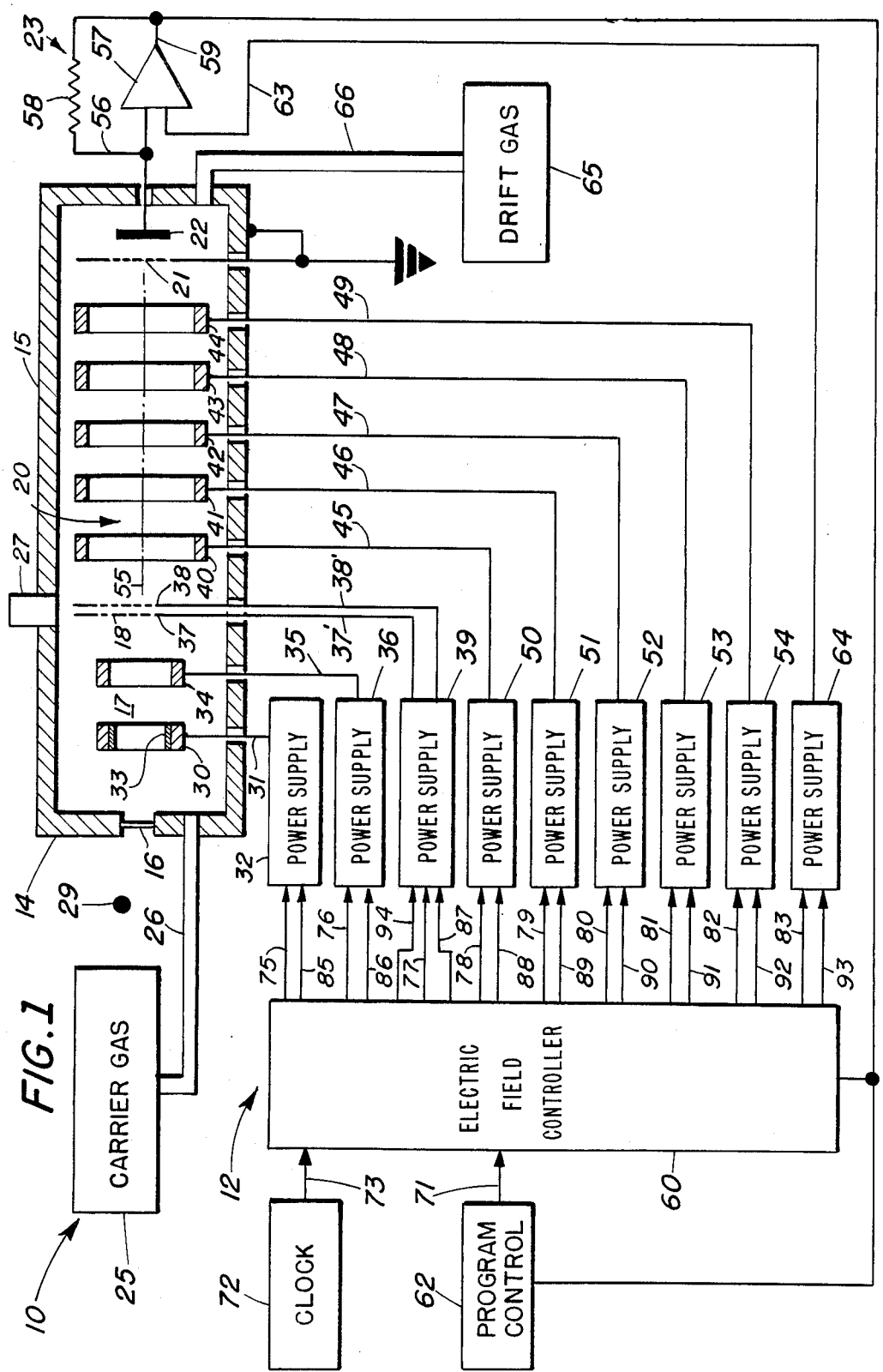
FIG. 1 is a cross section and schematic view of one embodiment of the invention.

Referring to FIG. 1, an ion mobility spectrometer 10 is shown which includes circuitry 12 for controlling the electric field within ion mobility spectrometer cell 14. An ion mobility spectrometer cell 14 is conventional in the art and may be, for example, an ion mobility spectrometer cell as shown in U.S. Pat. No. 4,378,499 which is incorporated herein by reference. Ion mobility spectrometer cell 14 has an inlet 16 which may be, for example, a membrane, a reaction region 17, a shutter grid 18, a drift region 20 an aperture grid 21, a collector 22 and detection circuit 23. A carrier gas 25 which may be, for example, nitrogen, pure air with or without water vapor may flow through tube 26 into reaction region 17 and out through port 27. Carrier gas 25 may scrub the inside of membrane 16 prior to passing through reaction region 17. A sample gas 29 may enter reaction region 17 by way of membrane 16. Source ring 30 is coupled over line 31 to an output of power supply 32. Source ring 30 may contain foil 33 which may be, for example, nickle 63 to provide a radiation source for creating ions from carrier gas 25 and sample gas 29. Ring 34 may be coupled over line 35 to an output of power supply 36. Source ring 30 and ring 34 function to generate an electric field in reaction region 17 to move ions of positive or negative polarity toward drift region 20. Shutter grid 18, which may have a first grid 37 and a second grid 38, are coupled over lines 37' and 38' to respective outputs of power supply 39.

Drift region 20 has rings 40 through 44, which are coupled over lines 45 through 49, respectively, to the output of power supplies 50 through 54, respectively. Rings 40 through 44 function to generate an electric field in drift region 20 substantially parallel to longitudinal axis 55. Aperture grid 21 is coupled to ground potential and collector 22 is coupled over lead 56 to an input of amplifier 57 and to one side of resistor 58. The output of amplifier 57 is coupled to the other side of resistor 58 and over lead 59 to an input of electric field controller 60 and an input of program control 62. A second input of amplifier 57 is coupled over lead 63 to an output of power supply 64. Power supply 64 functions to apply a voltage such as $+15$ V or $-15$ V to keep collector 22 at $+15$ V or $-15$ V with respect to ground potential.

Drift gas 65 which may be, for example, nitrogen, air, etc. is coupled over tube 66 to a second end of drift region 20 and flows through drift region 20 to shutter grid 18 and exits by way of port 27. Housing 15 functions to contain the gasses within ion mobility spectrometer cell 14 and to keep other gasses from entering.

Program control 62 has an output coupled over lead 71 to an input of electric field controller 60. Program control 62 functions to give electric field controller 60 instructions which electric field controller 60 may interpret.

The instructions, for example, may address a memory in electric field controller 60, for example, a read only memory which may provide a plurality of polarity signal and signals indicative of voltages to be coupled to power supplies 32, 36, 39, 50–54 and 64. Alternately the instructions may set a counter which in turn generates a sequence of addresses for the memory. Program control 62 may respond to signals on line 59 to generate instructions for electric field controller 60 for detection of certain ions, to perform chemical reactions, built in test and calibration.

A clock 72 functions to provide real time clock signals over lead 73 to an input of electric field controller 60. Electric field controller 60 couples polarity signals over leads 75 through 83 to power supplies 32, 36, 39, 50–54 and 64, respectively. Electric field controller 60 functions to provide signals indicative of voltage over leads 85 through 93 to a voltage input of power supplies 32, 36, 39, 50–54 and 64. Power supplies 32, 36, 39, 50–54 and 64 function to respond to the respective polarity signal and respective signal indicative of voltage to provide an output voltage of the corresponding polarity and magnitude at its output. The rise and fall times of the outputs of power supplies 32, 36, 39, 50–54 and 64 may be controlled, for example, to ten microseconds in switching from one voltage of one polarity to a second voltage of a secind polarity. For example, power supply 32 may switch from +850 V to −850 V. Electric field controller 60 provides a shutter grid control signal over lead 94 to an input of power supply 39. Power supply 39 functions to place the voltages on leads 37 and 38 at the same potential at times a control pulse is coupled over lead 94 which opens shutter grid 18 to permit ions from reaction region 17 to flow into drift region 20.

In the conventional operation of ion mobility spectrometer cell 14, voltages are placed on source ring 30, rings 34, 40–44 and aperture grid 21 as shown in Table I to cause either corresponding positive or negative ions to move toward collector 22. The length of drift region 20 may be 4.12 cm and aperture grid 21 may be spaced 0.10 cm from collector 22. The resulting electric field in drift region 20 may be, for example, 145 V per cm. Membrane 16 may pass molecules in the range between 100 to 500 atomic mass units (AMU), corresponding to a reduced mobility $K_0$ of approximately three to one.

$$K_0 = \frac{Cl}{Et} \quad (1)$$

In equation (1), $K_0$ is the reduced mobility. E is the electric field. t represents time. l represents length along longitudinal axis 55 from shutter grid 18 to collector 22 and C represents a constant shown by equation (2).

$$C = \frac{P}{P_S} \times \frac{T_A}{T} \quad (2)$$

In equation (2) P represents pressure, $P_S$ represents standard pressure such as an atmospheric pressure, T represents temperature, for example, 70° C. and $T_A$ represents absolute temperature, for example, 273° C. The measurements shown by the various figures were made at 70° C. in the drift region. The drift time of an ion having a $K_0=2$ is 13 ms. The drift time of an ion having an ion mobility $K_0=1.4$ is 18 ms.

A new method of increasing the sensitivity of an ion mobility spectrometer 10 to ions below a selected $k_0$ is shown in FIGS. 5, 6 and 7. First, however, a carrier gas and sample gas enters reaction region 18 where ions are generated therefrom by a nickle 63 source. The electric field in the reaction region causes the ions to move toward shutter grid 18. A forward electric field in drift region 20 from time $T_0$ to $T_1$ is shown by curve 105 in FIG. 5. At time $T_0$ shutter 18 is pulsed open to allow the ions to enter drift region 20 as shown by curve 106 in FIG. 6. The ions move toward collector 22 and separate according to their mobility with the more mobile ions reaching collector 22 first. As the ions of interest of a predetermined mobility approach collector 22, the electric field is reversed as shown by curve 105 in FIG. 5 at $T_1$. The ions of interest and ions of lower mobility reverse their travel and drift back along longitudinal axis 55 toward shutter grid 18. Note, that only ions with a selected maximum $K_0$ and less are now in drift region 20. These trapped ions will come together just in front of shutter grid 18 at time $T_2$. The time required to drift back to the shutter grid $T_2-T_1$ is the same as that time required to drift forward $T_1-T_0$ if the electric fields are equal in the forward and reverse directions. At time $T_2$,

TABLE I

| | Source Ring 30 | Ring 34 | Shut. Grid 18 | Ring 40 | Ring 41 | Ring 42 | Ring 43 | Ring 44 | Aprt. Grid 21 | Col. 22 |
|---|---|---|---|---|---|---|---|---|---|---|
| +Ions | 850 | 700 | 600 | 500 | 400 | 300 | 200 | 100 | 0 | −15 V |
| −Ions | −850 | −700 | −600 | −500 | −400 | −300 | −200 | −100 | 0 | +15 V |

FIG. 2 is a curve showing a forward electric field applied in the drift region 20 without any change over time. In FIG. 2, the ordinate represents time and the abscissa represents electric field. Curve 100 shows the electric field is in the forward direction. FIG. 3 shows a curve 101 which may be the signal on line 94 to open and close shutter grid 18. In FIG. 3, the ordinate represents time and the abscissa represents open and closed condition of shutter grid 18. FIG. 4 shows curves 102 through 104 corresponding to reduced mobilities $K_0$ equal to 1, 2 and 3, respectively. In FIG. 4, the ordinate represents time and the abscissa represents distance in drift region 20 from shutter grid 18 to collector 22.

The movement of ions in drift region 22 under the influence of electric field may be represented by equation (1).

just before the trapped ions hit shutter grid 18, the electric field in drift region 20 is again reversed as shown by curve 105 in FIG. 5 so that the ions start moving in the forward direction again toward collector 22 and, at the same time, the shutter grid 18 is pulsed open as shown by curve 106 in FIG. 6 at time $T_2$ a second time. This doubles the concentration of selected ions in drift region 20. In other words, while the selected ions are graveling in reverse direction, reaction region 17 was continuing to generate ions and had an appropriate electric field to move the ions to shutter grid 18. At time $T_2$ the ions generated during the inverval from time $T_1$ to $T_2$ enter the drift region and join the ions that entered the drift region at time $T_0$. Again, as the selected ions approach collector 22, the electric field may be again reversed and the sequence repeated until the desired concentration of selected ions is achieved in drift region 20.

The appropriate potentials on source ring 30, ring 34, shutter grid 18, rings 40–44, aperture grid 21 and collector 22 is shown in Table II for positive ions and negative ions.

TABLE II

|  | Source Ring 30 | Ring 34 | Shut. Grid 18 | Ring 40 | Ring 41 | Ring 42 | Ring 43 | Ring 44 | Aprt. Grid 21 | Col 22 |
|---|---|---|---|---|---|---|---|---|---|---|
| −Ions |  |  |  |  |  |  |  |  |  |  |
| $T_0$-$T_1$ | −850 | −700 | −600 | −500 | −400 | −300 | −200 | −100 | 0 | +15 V |
| $T_1$-$T_2$ | +350 | 500 | 600 | 500 | 400 | 300 | 200 | 100 | 0 | +15 V |
| $T_2$-$T_5$ | −850 | −700 | −600 | −500 | −400 | −300 | −200 | −100 | 0 | +15 V |
| +Ions |  |  |  |  |  |  |  |  |  |  |
| $T_0$-$T_1$ | 850 | 700 | 600 | 500 | 400 | 300 | 200 | 100 | 0 | −15 V |
| $T_1$-$T_2$ | −350 | −500 | −600 | −500 | −400 | −300 | −200 | −100 | 0 | −15 V |
| $T_2$-$T_5$ | 850 | 700 | 600 | 500 | 400 | 300 | 200 | 100 | 0 | −15 V |

Referring to FIG. 7 at time $T_0$, ions of mobility $K_0 = 1, 2, 3$ enter drift region 20 as shiown by curves 107 through 109, respectively. Prior to time $T_1$, the ions of mobility $K_0 = 3$ reach collector providing an output signal on line 59. At time $T_1$, the electric field in drift region 20 is reversed causing ions of mobility $K_0 = 1, 2$ to flow toward shutter grid 18. If the electric field in the forward direction is equal to the electric field in the reverse direction, then ions of mobility $K_0 = 1, 2$ will both reach shutter grid 18 or just in front of shutter grid 18 at time $T_0$ as shown by curves 107 and 108. At time $T_2$, additional ions pass through open shutter grid 18 and join the ions just in front of shutter grid 18 and drift toward collector 22 as shown by curves 110 through 112 for ions of mobility $K_0 = 1, 2, 3$ respectively.

A method of detecting ions of incremental mobility is described in FIGS. 8 through 10. By making the reverse linear field of the same amplitude but of shorter duration then the forward linear field, the ions will have a net forward motion for each forward and reverse cycle of the field. A desired increment of mobility $K_0$'s can therefore be collected by collector 22 after a desired number of field reversals shown by curve 115 in FIG. 8. Curve 116 in FIG. 9 shows that shutter grid 18 is opened only once at time $T_0$. Curves 117 through 120 show typical ion travel in drift region 20 with the electric field reversals as shown in FIG. 8. The mobility $K_0$ of ions detected between $T_0$ and $T_2$ is shown by equation (3). The mobility of ions detected between time $T_3$ and $T_5$ is shown by equation (4). The mobility of ions collected between times $T_6$ and $T_8$ is shown by equation (5). The mobility of ions collected between $T_9$ and $T_{11}$ is shown by equation (6).

$$K_0 > \frac{C}{E} \frac{l_1}{2 t_l} \quad (3)$$

$$\frac{Cl_1}{E}\left(\frac{l}{2 t_1}\right) > K_0 > \frac{Cl_1}{E}\left(\frac{l}{3 t_1}\right) \quad (4)$$

$$\frac{Cl_1}{E}\left(\frac{l}{3 t_1}\right) > K_0 > \frac{Cl_1}{E}\left(\frac{l}{4 t_1}\right) \quad (5)$$

$$\frac{Cl_1}{E}\left(\frac{l}{4 t_1}\right) > K_0 > \frac{Cl_1}{E}\left(\frac{l}{5 t_1}\right) \quad (6)$$

The same desired increment of ions with mobility $K_0$'s can also be collected by collector 22 in increments using equal time increments but with the reversed electric field of lower intensity.

Figure 11:
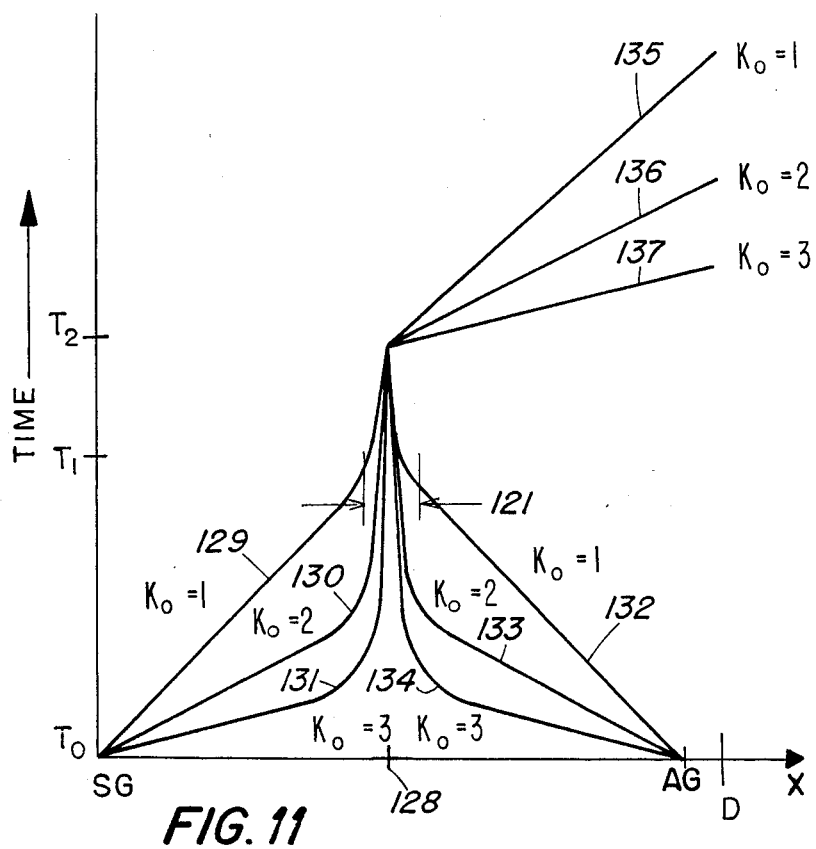
Figure 12:
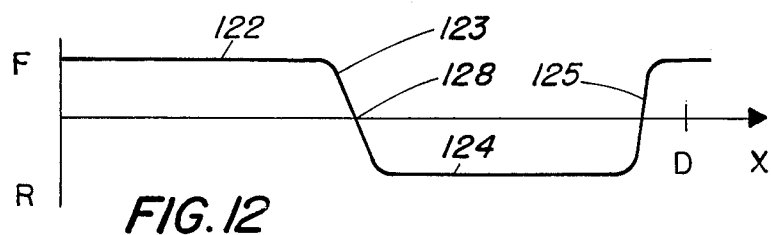
Figure 13:
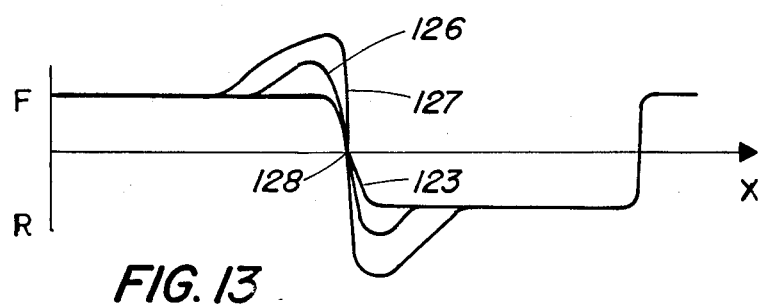
Figure 14:
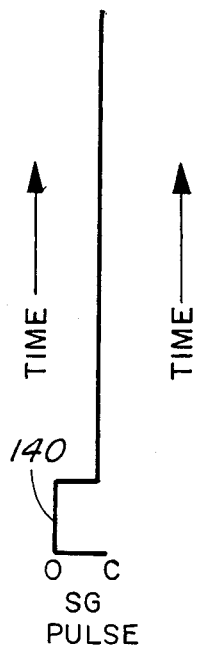
Figure 15:
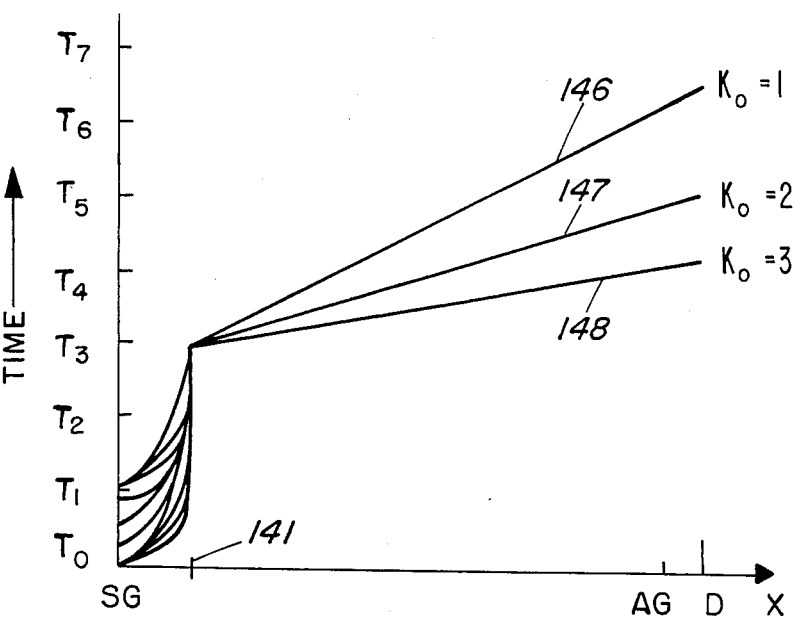

An electric sequence that will negate the past history of the mobility of ions that are trapped in drift region 20 by positioning the ions in drift region 20 at a particular location along longitudinal axis 55 is described in FIGS. 11 through 13. As shown in FIG. 12, a constant forward electric field extends from shutter grid 18 to a predetermined distance along longitudinal axis 55 in drift region 20 shown by curve 122. A transition region 121 where the electric field goes from the forward direction to the reverse direction at a particular location along longitudinal axis 55 is shown by curve 123 in FIG. 12. On the other side of transition region 121 shown by the curve 123, the electric field is in the reverse direction for a predetermined distance almost to aperture grid 21 as shown by curve 124. Beyond aperture grid 21 to collector 22 a forward electric field exists due to the potential of collector 22 which is −15 V for position ions and +15 V for negative ions with respect to aperture grid 21 which is normally at 0 V. Curve portion 125 shows the forward electric field between aperture grid 21 and collector 22.

With the static electric field in drift region 20 as shown by FIG. 12 from time $T_0$ to time $T_1$, ions of mobility $K_0 = 1, 2, 3$ drift from as far as shutter grid 18 or aperture grid 21 to the transition region shown by curve 123. Transition region 121 shown in FIG. 11 functions to provide an ion well in drift region 20. At time $T_1$ the magnitude of the electric field on either side of the ion well or transition region 121 is increased such as from curve 123 shown also in FIG. 13 to curve 126 and then to curve 127 at time $T_2$. The ion in the field transition region 121 will be compressed as shown in FIG. 11 at time $T_2$ at position 128 along longitudinal axis 55. Curves 129 through 132 show the ions in drift region 20 compressing to position 128 from time interval $T_1$ to $T_2$. At time $T_2$ a forward electric field is then applied to drift region 20 to allow the ions to drift toward collector 22 as shown in FIG. 11 by curves 135 through 137. The forward electric field may have a constant magnitude from shutter grid 18 to aperture 21. When the ions in drift region 20 are compressed, the higher mobility ions tend to migrate to the ring surface because of mutual charge repulsion. This produces a slightly higher concentration of the higher AMU's in the drift region.

In conventional ion mobility spectrometry with only a forward electric field in the drift region 20, the shutter grid pulse length determines the resolution between ions of various mobilities $K_0$'s and the minimum detectable concentration of ions of a particular mobility $K_0$. By using the above electric field sequence as shown in FIGS. 11 through 13 and a long shutter grid pulse, the resolution of ions of various mobility $K_0$ becomes a function of the compressing field strength shown by curve 127 in FIG. 13. The sensitivity becomes a function of the shutter grid pulse length since all the ions in drift region 20 and the ions entering drift region 20 from shutter grid 18 will be collected in the ion well at position 128. In conventional ion mobility spectrometry, there is a limit to the shutter grid pulse length and the resulting concentration of ions that a conventional IMS structure can control. In fact, the ion well at transition region 121 and the compression of ions to position 128 may serve the function of a shutter grid.

FIGS. 14 through 17 show curves for carrying out the function of a shutter grid. The shutter grid is open from time $T_0$ to time $T_1$ as shown by curve 140 in FIG. 14. From time $T_0$ to time $T_2$ ions are collected at position 141 by the transition in the electric field from a forward direction to a reverse direction shown by curve portion 142. From time $T_2$ to time $T_3$ the magnitude of the electric field on either side of position 141 is increased as shown by curves 143 through 145 in FIG. 17 which compresses the ions of various mobility to position 141 on longitudinal axis 55. At time $T_3$ a forward electric field of constant magnitude is provided in drift region 20 to cause ions of mobility $K_0=1, 2, 3$ to drift to collector 22 as shown by curves 146 through 148, respectively.

Figure 16:
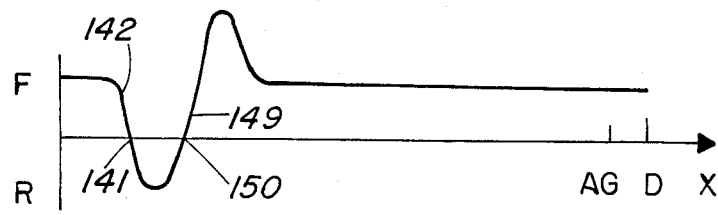
Figure 17:
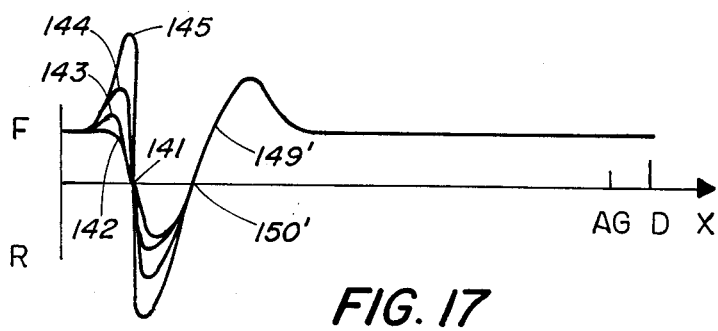

Referring to FIG. 16, at times $T_0$ to $T_2$ ions on the left of position 150 will be affected by a reverse electric field and flow back toward position 141. Ions to the right of position 150 will be influenced by a forward electric field shown by curve 149 and will drift in the forward direction to collector 22.

The potential of source ring 30, ring 34 and 40 through 44, aperture grid 21 and collector 22 is shown in Table III during the time periods $T_0$ to $T_2$, $T_2$ to $T_3$ and $T_3$ and later.

faster than the other ions to reach collector 22 at an earlier time.

Figure 21:
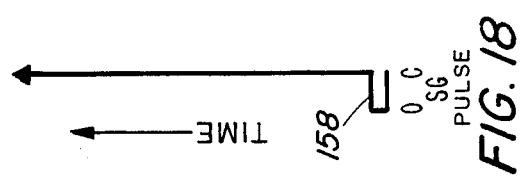
Figure 23:
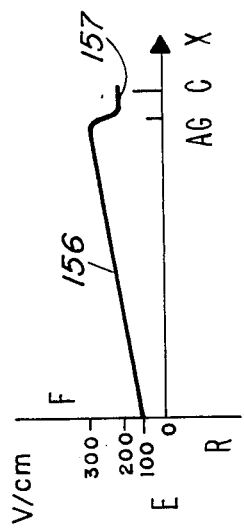

FIG. 23 shows curve 164 decreasing from 300 V per cm to 100 V per cm from shutter grid 18 to aperture grid 21. Curve portion 165 shows a constant electric field between aperture grid 21 and collector 22. Curve 166 in FIG. 21 shows the time when shutter grid 18 is open. Curves 167 to 169 show the position as a function of time for ions of various mobilities $K_0=1, 2, 3$, respectively, as they drift toward collector 22. As the ions progress from shutter grid 18 to aperture grid 21 they slow down, taking more time to reach collector 22.

A sequence of forward and reverse non-linear electric fields (increasing or decreasing magnitude), may be used for trapping and isolating a selected ion having a mobility $K_0$. At time $T_0$ shutter grid 18 opens as shown by curve 172 in FIG. 24 which admits ions into drift region 20. A forward electric field of constant magnitude will cause the ions to drift toward collector 22 as shown by curves 173 through 175 for ions of mobility $K_0=1, 2, 3$, respectively. At time $T_1$ a non-linear field as shown in FIG. 26 may be generated in drift region 20 to cause ions of mobility $K_0=1$ and $K_0=2$ to reverse direction toward shutter grid 18. Prior to time $T_1$ ions of mobility $K_0=3$ had reached collector 22 as shown by curve 175. With the reverse field, the ions move toward shutter grid 18 with the magnitude of the electric field increasing as they approach shutter grid 18 causing ions having mobility $K_0=1$ to reach shutter grid 18 and to be neutralized prior to time $T_2$. At time $T_2$ the electric field is reversed with a constant forward electric field causing ions having mobility $K_0=2$ to drift to collector 22 whereupon at a later time they reach collector 22. Thus, as shown in FIG. 25, ions of mobility $K_0=3$ or greater reach collector 22 prior to time $T_1$ and are eliminated from drift region 20 and prior to time $T_2$ ions of mobility $K_0=1$ or less reach a shutter grid 18 where it

TABLE III

| | Source Ring 30 | Ring 34 | Shut. Grid 18 | Ring 40 | Ring 41 | Ring 42 | Ring 43 | Ring 44 | Aprt. Grid 21 | Col. 22 |
|---|---|---|---|---|---|---|---|---|---|---|
| +Ions | | | | | | | | | | |
| $T_0$–$T_2$ | 850 | 700 | 600 | 500 | 400 | 300 | 200 | 100 | 0 | −15 V |
| $T_2$–$T_3$ | 850 | 700 | 600 | 0 | 600 | 300 | 200 | 100 | 0 | −15 V |
| $T_3$–$T_7$ | 850 | 700 | 600 | 500 | 400 | 300 | 200 | 100 | 0 | −15 V |

Figure 19:
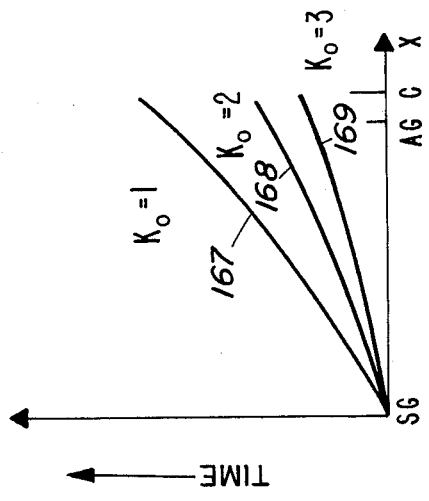
Figure 18:
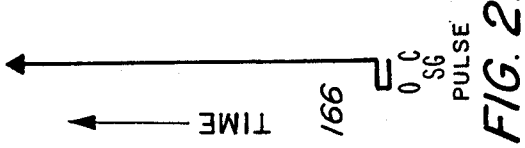
Figure 22:
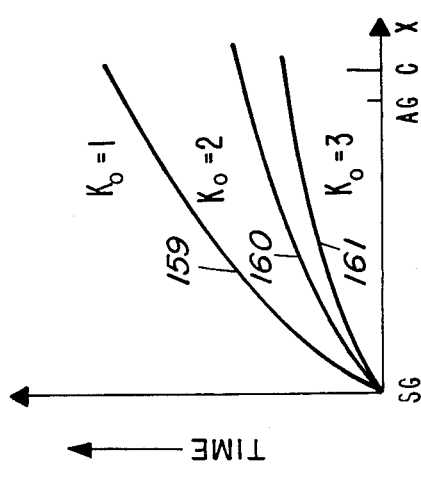
Figure 20:
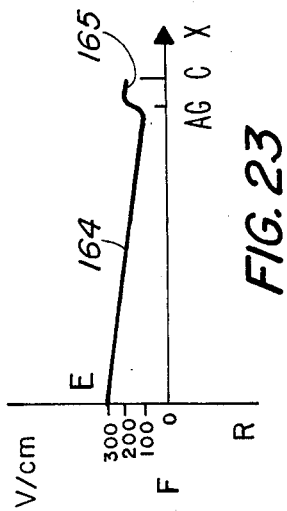

Non-linear electric fields or electric fields with increasing or decreasing magnitude may be used to increase the resolution or separation between ions with various mobilities $K_0$'s. The non-linear electric fields in the drift region 20 consist of increasing or decreasing the electric field magnitude in the direction of ion motion as shown in FIG. 20 by curve 156. In FIG. 20 the electric field increases from 100 V/cm to 300 V/cm from shutter grid 18 to aperture grid 21. The electric field from aperture 21 to collector 22 is constant as shown by curve portion 157. An electric field in the range from 50 V per cm to 300 V per cm has been used. Also, linearly and exponentially changing electric fields as a function distance along longitudinal axis 55 in drift region 20 have been tried. Curve 158 in FIG. 18 shows the opening of shutter grid 18 to permit ions into drift region 20. Curves 159 to 161 in FIG. 19 show the position as a function of time for ions of various mobilities $K_0=1, 2, 3$, respectively. With an increasing magnitude of the electric field, the ions of highest mobility travel picks up a charge and flows with drift gas 67 out port 27. Thus, ions of mobility $K_0=2$ are remaining in drift region 20 having been trapped and isolated.

Figure 27:
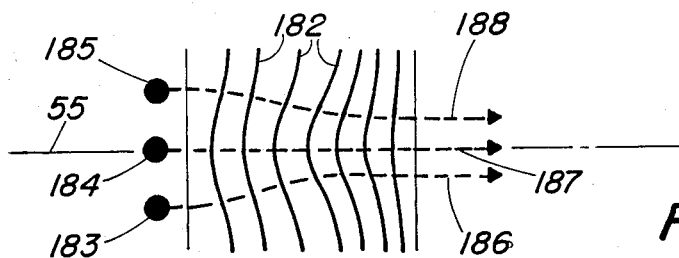
Figure 28:
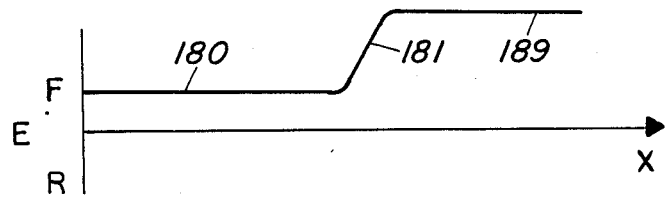

Ions of various mobility may be focused along longitudinal axis 55 away from the edges of rings 40 to 44 by applying an electric field in drift region 20 as shown by curve 180 in FIG. 28. The focusing of ions back to longitudinal axis 55 of drift region 20 becomes more important as the time spent by ions of a desired mobility $K_0$ in drift region 20 increases. A large increase in the electric field strength shown by curve portion 181 in FIG. 28 in the direction of ion travel will cause the equal potential surfaces in drift region 20 to dimple toward the direction of lower electric fields as shown in FIG. 27 by equal potential lines 182. Ions 183 through 185 passing through perpendicular to these dimpled equal potential surfaces 182 will then be brought from the edges close to rings 40 through 44 toward the center of drift region 20 to longitudinal axis 55 as they move in drift region 20. The path of ions 183 to 185 is shown by broken lines 186 through 188, respectively, curve portion 189 in FIG. 28 shows a region of increased electric field. In FIG. 27 the ordinate represents distance orthogonal to longitudinal axis 55 and the abscissa represents distance parallel to longitudinal axis 55 of ion mobility spectrometer cell 14.

A focusing sequence can be applied in either forward or reverse direction and whenever it is felt a sufficient quantity of ions has migrated out of the center of drift region 20. A non-linear increasing field allows ions to remain in close axial proximity for a longer time when the electric field is low. A loss of selected ions' positional control may result due to the concentration of other ions of other mobilities $K_0$'s. A linear electric field should be applied for a short time duration to separate ions of dissimilar mobility $K_0$'s axially or along longitudinal axis 55 prior to the application of a non-linear increasing electric field.

By using the above non-linear electric field technique in appropriate timed sequences, IMS/IMS can be achieved in drift region 20. The IMS/IMS technique provides the user with a more positive identification of the ionized molecules that have a similar mobility $K_0$ but dissimilar atomic mass unit and fracturing energy levels. A fracturing energy level is the threshold energy for dissociative ionization with daughter ions or fragment ions being formed.

Figure 29:
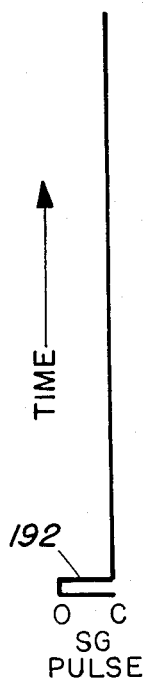
Figure 30:
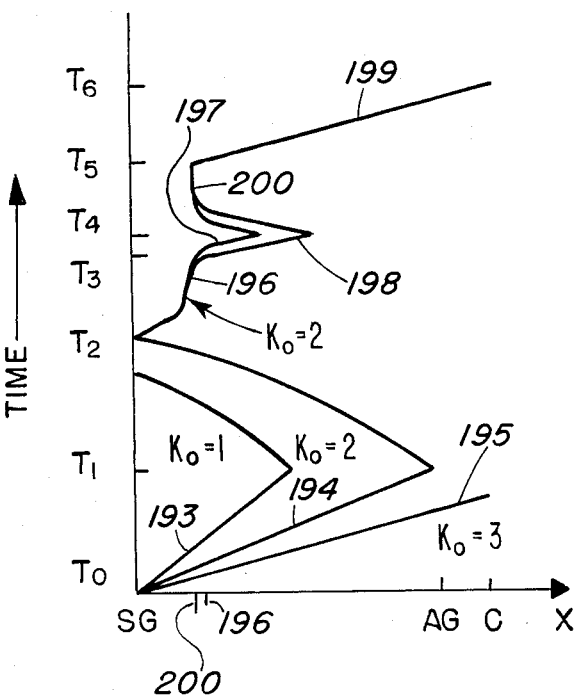

Referring to FIGS. 29 and 30, at time $T_0$ shutter grid 18 opens as shown by curve 192 in FIG. 29 to admit ions into drift region 20 which are allowed to drift toward collector 22 under a forward electric field of constant magnitude. Curves 193 through 195 show the position as a function of time of ions having mobility $K_0=1, 2, 3$. At time $T_1$ the electric field is reversed in drift region 20 with the electric field increasing as the ions approach shutter gate 18 as shown by curves 193 and 194. At time $T_2$ an ion well is formed in drift region 20 to collected all ions to a certain position followed by increasing the electric field on either side of the position to compress the ions to position 196 shown in FIG. 30. It is noted that the ions in the ion well were isolated from other ions to have a particular ion mobility such as $K_0=2$.

The selected ions are then fractured. This is achieved in several ways, depending on the energy required to fracture the particular molecule. The intent is to identify the presence of a particular ionized chemical in the original sample admitted at time $T_0$ into drift region 20 and to differentiate that particular chemical from other chemicals with similar mobilities $K_0$'s. It may be necessary to apply a fracturing energy below that required to fracture the desired chemical to fracture other chemicals first and eliminate those by-products prior to testing for the presence of the desired chemical. One method of fracturing the ion of selected mobility $K_0$ is by applying a high electric field such that the ions will try to move at a velocity in excess of that achievable in the presence of drift gas 65 shown in FIG. 1. Another method is to apply an alternating electric field or reversing electric field on either side of the trapped ion of mobility $K_0$ and cause collisions between the ions as they move back and forth along longitudinal axis 55 in the vicinity of position 196. Higher fracturing energy levels, if required, can be achieved using an arc discharge by means of electrodes in drift region 20 or by ultra violet emission from an ultra violet source within or through a window to drift region 20.

After the ions are fractured, an ion well is re-established to compress at position 200 the newly formed ions that will have a different mobility $K_0$ than those originally trapped at position 196. After the new ions are positioned at position 200, the field is changed to a constant forward electric field allow the new ions to drift and separate according to their mobility and be detected at collector 22.

As shown in FIG. 30, the ions are fractured from time $T_3$ to $T_4$ to provide ions of various mobility shown by curves 197 and 198. The ions are collected in an ion well and compressed to position 200 as shown by curves 197 and 198 from time $T_4$ to $T_5$. At time $T_5$ a forward linear electric field is provided in drift region 20 to allow the ions to drift toward collector 22 during the time intervals from $T_5$ to $T_6$ whereupon the new ions having a new mobility $K_0$ are detected as shown by curve 199. It is noted that while ions of one polarity are compressed during times $T_4$ to $T_5$, the ions of the other polarity are dispersed toward shutter gate 18 and collector 22 or collected in a second ion well. Thus, ions of only one polarity will be collected in the ion well prior to measuring their drift time to collector 22.

The simultaneous trapping of selected positive and negative ions in drift region 20 and then causing them to co-exist axially for a chemical reaction is an extension of plasma atmospheric chemistry that offers both control and specificity. The sequence of electric fields in drift region 20 to achieve a chemical reaction is shown in FIGS. 31 through 33. At time $T_0$ shutter grid 18 is pulsed as shown by curve 201 to admit ions into drift region 20. The ions of various mobilities such as $K_0=1a$, $2a$ and $3a$ are allowed to drift in drift region 20 as shown by curves 202 through 204, respectively. At time $T_1$ a reverse electric field is applied to drift region 20 with the field increasing as it nears shutter grid 18 to eliminate ions of mobility $K_0=1a$ or less. At time $T_2$ a forward electric field is applied to drift region 20 to move ions having mobility $K_0=2a$ near collector 22 where they are held in an ion well at position 205 shown in FIG. 32. During the times from $T_0$ to $T_3$, the field in reaction region 17 is changed to allow the opposite polarity ions to drift toward shutter grid 18. At time $T_3$ the drift region is operated in two sections with the right side of drift region 20 near position 205 holding ions of mobility $K_0=2a$. At time $T_3$ shutter grid 18 is opened as shown by curve 201 to admit ions of opposite polarity into drift region 20. These ions b are subjected to a forward linear field from $T_3$ to $T_4$ followed by a reversed electric field of increasing magnitude toward shutter grid 18 from time $T_4$ to $T_5$. The paths of ions of mobility $K_0=1b$, $2b$ and $3b$ are shown by curves 207 through 209 in FIG. 32.

At time $T_5$ ions b are attracted to an ion well and then compressed at position 210 as shown by curves 211 and 212. At time $T_6$ ions b of mobility $K_0=2b$ and $3b$ are subjected to a reverse linear electric field causing ions of mobility $3b$ to be neutralized by shutter grid 18 prior to time $T_7$ as shown by curve 214. At time $T_7$ an electric field of is placed across drift region 20 which causes ions b to move in the forward direction toward collector 22 and ions a to move in the reverse direction toward shutter grid 18 as shown by curves 216 and 217.

At time $T_8$ the ions of opposite polarity pass each other. The electric field intensity is reduced and reversed several times. As the positive and negative ions chemically combined, they are neutralized and leave the drift region with the drift gas 65 to port 27. The positive and negative ions may pass each other at position 218. The electric field provided after $T_8$ is shown in FIG. 33 with the electric field increasing and decreasing in the forward direction as shown by curve 220 and then increasing and decreasing in the reverse direction as shown by curve 221 then passing through zero and increasing and decreasing in the forward direction as shown by curve portion 222.

Figure 36:
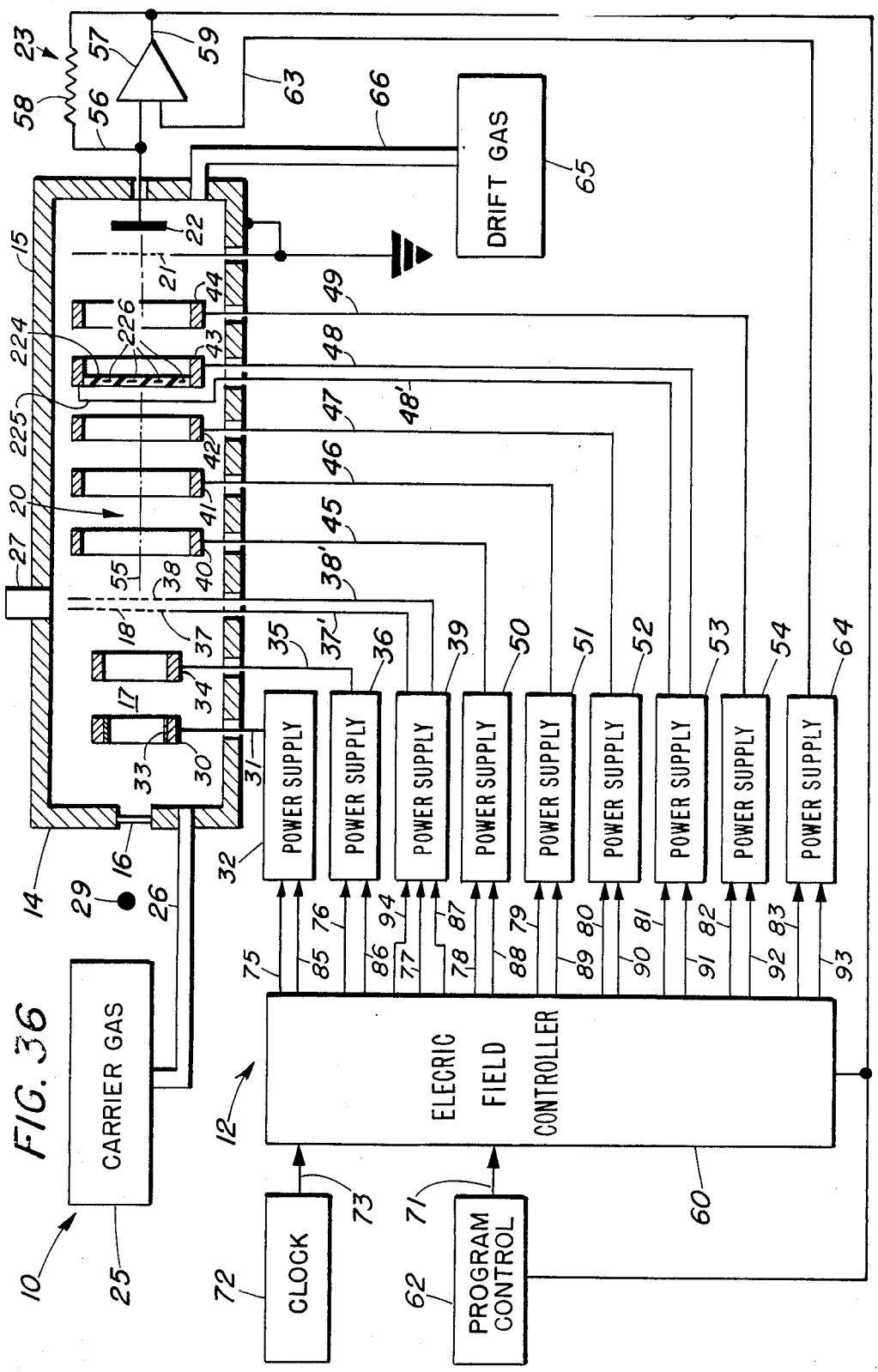
FIG. 36 is an alternate embodiment of the invention wherein the drift region 20 of FIG. 1 is modified.

A membrane 224 may be positioned in drift region 20 at position 218 to aid in the chemical reaction and act as a by-product repository as shown in FIG. 36. Membrane 224 could act as catalyst for the chemical reaction, or as a source or sink for the chemical reaction thermal requirements.

In FIGS. 2, 5, 8 and 33 the ordinate represents time and abscissa represents the electric field forward (F) and reverse (R). In FIGS. 3, 6, 9, 14, 18, 21, 24, 29 and 31 the ordinate represents time and abscissa represents shutter grid open (O) and closed (C) condition. In FIGS. 4, 7, 10, 11, 15, 19, 22, 25, 30 and 32 the ordinate represents time and the abscissa represents distance X. In FIGS. 12, 13, 16, 17, 20, 23, 26 and 28 the ordinate represents electric field and the abscissa represents distance X.

Figure 34:
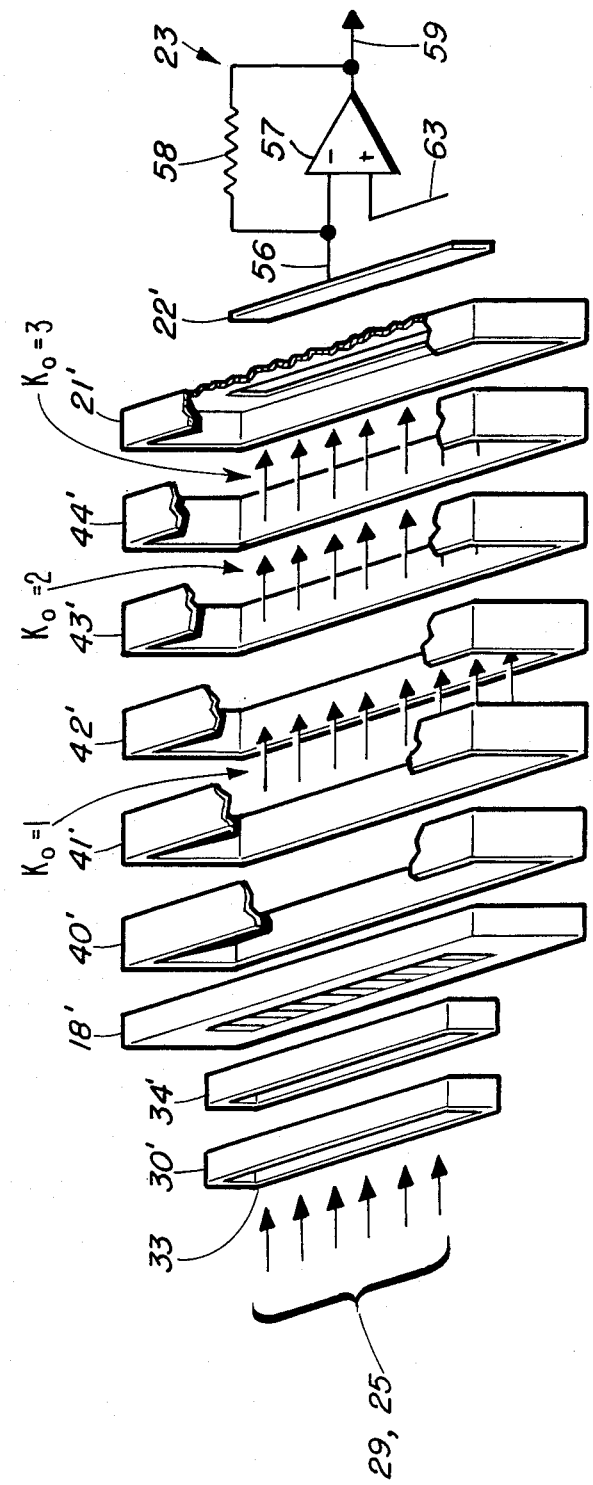
FIG. 34 is a first alternate embodiment of the invention.

FIG. 34 shows an alternate embodiment of the invention. In FIG. 34 like references are used for functions corresponding to the apparatus of FIG. 1. Prime numbers are used for functions corresponding to the apparatus of FIG. 1 with their physical shape modified. In FIG. 34 in place of rings which can control a limited quantity of ions, a two dimensional rectangular structure is shown which is scalable or may be increased in width or height to accommodate a large quantity of ions.

Figure 35:
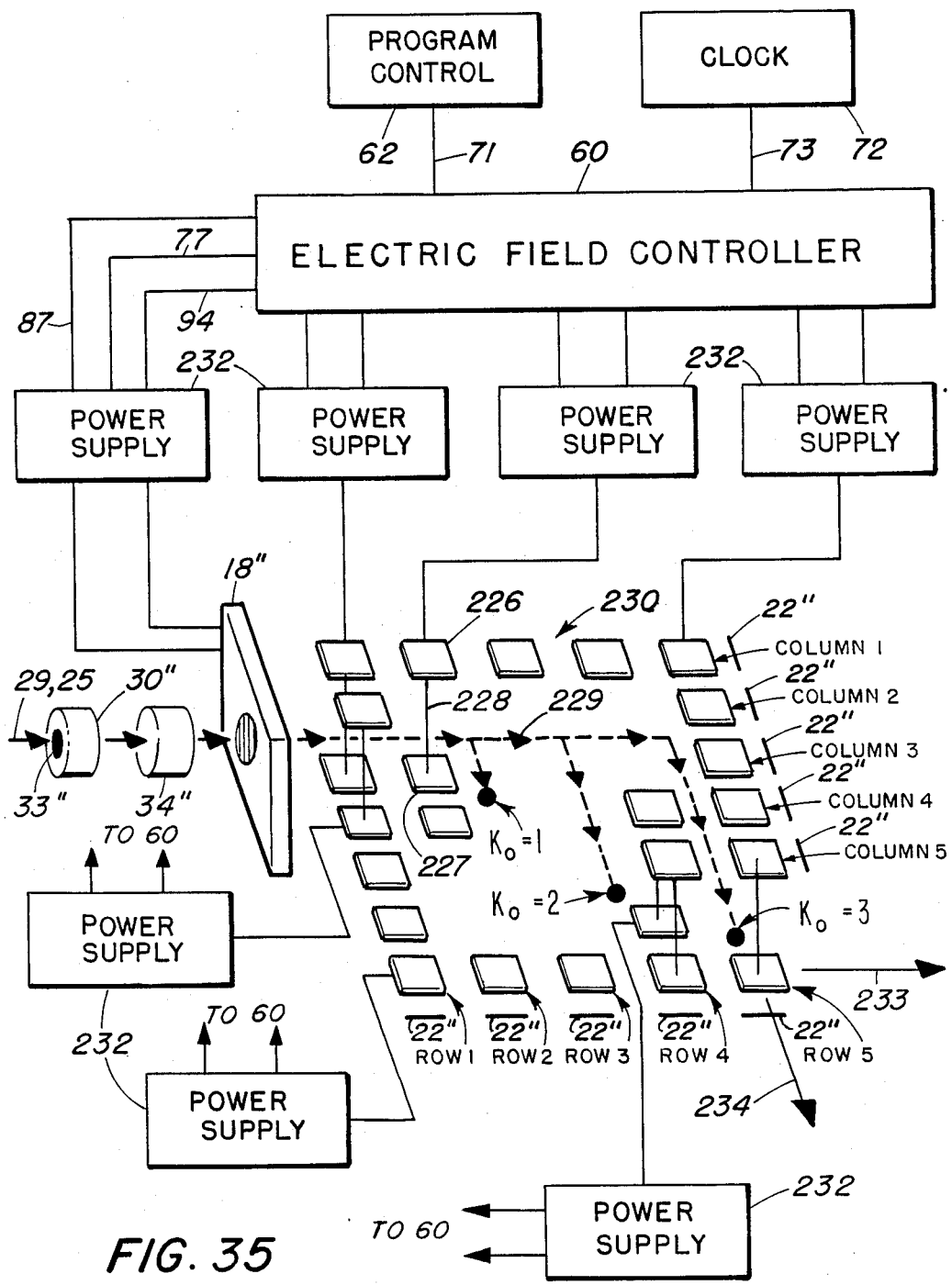
FIG. 35 is a second alternate embodiment of the invention.

FIG. 35 shows an alternate embodiment of the invention. In FIG. 35 like references are used for function corresponding to the apparatus of FIG. 1. Double prime numbers are used for functions corresponding to the apparatus of FIG. 1 with their physical shape modified. In FIG. 35 the rectangular electrodes of FIG. 34 are segmented as width as segments 230. Each segment 30 comprises an electrode pair 226 and 227 held at the same potential by conductor 228 which may be a rod or even a screw or bolt connecting the two electrodes directly. Each electrode segment 230 is coupled to a respective power supply 232 and each power supply is coupled to an electric field controller 60. The segments provide and X and Y or two dimensional directional control of ions.

In operation, carrier gas 29 and sample gas 25 pass through source ring 30" and ring 34" to shutter grid 18". At times when the shutter grid 18" is open, the ions under the influence of the electric field produced by the plurality of segments 230 move, for example, forward shown by path 229 wherein ions of mobility $K_0 = 1, 2$ and 3 are spaced apart in the X direction shown by arrow 233 by providing an electric field of constant magnitude in the X direction. Subsequently, with the shutter grid closed, an electric field may be placed in the Y direction shown by arrow 234 to cause ions of various mobility to travel along respective rows 3–5. After a period of time, ions of a selected mobility will be positioned under a respective electrode segment 230 (between its electrode pair) corresponding to a row and column. The technique for applying the electric field in the embodiment of FIG. 1 may be applied to the embodiment in FIG. 35 to completely control the ions within the plurality of segments 230. A collector may be positioned transverse to an electrode segment at the end of each column and row.

The embodiment shown in FIGS. 34 and 35 are suited for use with a magnetic field perpendicular to the plane of ion travel or motion. Just as a constant electric field produces a constant velocity of the ions, a constant magnetic field B will cause a constant side (orthogonal) velocity of the ions with respect to the forward velocity analogous to Hall semiconductor devices. Separation of ions of various mobilities $K_0$'s is then achieved in a two dimensional plane in a continuous instead of a batch process. With a magnetic field, collector 22' in FIG. 34 may be replaced by a plurality of collectors positioned to intercept collected ions. A point ion source as shown in FIG. 35 FIG. 35 by ring 30" and 34" shutter grid 18" should be used.

A method and apparatus for detecting ions has been described comprising an inlet for introducing a carrier gas and a sample gas into a reaction region, means for generating ions such as by a corona, ultra violet radiation source from the carrier gas and sample gas in the reaction region, means for generating an electric field in the reaction region to move the ions toward a drift region having a longitudinal axis, means for generating an electric field in the drift region substantially parallel or non-parallel, divergent or convergent to the longitudinal axis to control the position of selected ions in the drift region by applying electric fields in the forward and reverse direction with respect to the longitudinal axis. The electric fields may have increasing or decreasing magnitude as a function of distance from the shutter grid to the collector and vice versa from the collector to the shutter grid or may have transitions from forward to reverse direction.

The invention claimed is:

1. Apparatus for detecting ions comprising,
   a first inlet means for introducing a carrier gas and a sample gas into a reaction region,
   a second inlet means for introducing a drift gas into a drift region and at a pressure wherein the mean free path of the drift gas is a small fraction of the dimensions of the drift region,
   first means for generating first ions from said carrier gas and sample gas in said reaction region; second means for generating an electric field in said reaction region to move said first ions toward said drift region having a longitudinal axis, third means for generating an electric field in said drift region substantially parallel to said longitudinal axis to move said first ions toward a collector at first times, for generating an electric field in said drift region substantially parallel to a longitudinal axis to move said first ions away from said collector at second times, and
   for generating an electric field in said drift region substantially parallel to said longitudinal axis to move said first ions toward said collector at third times.

2. The apparatus of claim 1 wherein said second means for generating an electric field in said reaction region includes means for generating an electric field in said reaction region during said first and second times to move second ions of a first polarity toward a shutter for holding said second ions, said shutter including means for releasing said second ions of first polarity into said drift region at the beginning of third times to join with said first ions in said drift region.

3. Apparatus for detecting ions comprising:
   first inlet means for introducing a carrier gas and a sample gas into a reaction region, a second inlet means for introducing a drift gas into a drift region and at a pressure wherein the mean free path of the drift gas is a small fraction of the dimensions of the drift region, first means for generating ions from said carrier gas and sample gas in said reaction region, second means for generating an electric field in said reaction region to move said ions toward a first end of a drift region having a second end and a longitudinal axis, third means for generating an electric field in said drift region substantially parallel to said longitudinal axis, said electric field at first times having a first direction at said first end to accept ions from said reaction region, and a transition region between said first and second ends where said electric field reverses direction with respect to said first direction to provide an ion well for holding ions, said electric field in said drift region at second times having said first direction from said first end to said second end to move said ions toward a collector.

4. The apparatus of claim 3 wherein said third means for generating an electric field in said drift region includes fourth means for increasing the magnitude of the electric field in said transition region at third times prior to said second times to compress said ions within a shorter distance along said longitudinal axis in said transition region.

5. Apparatus for identification of ionized molecules having a similar mobility ($K_0$) but having dissimilar atomic mass units (AMU's) and fracturing energy levels comprising:

an inlet means for introducing a carrier gas and a sample gas into a reaction region, first means for generating ions from said carrier gas and sample gas in said reaction region, second means for generating an electric field in said reaction region to move said ions toward a first end of a drift region having a second end and a longitudinal axis, third means for generating a sequence of electric fields at predetermined times in said drift region substantially parallel to said longitudinal axis to isolate and position said ionized molecules having a similar mobility in said drift region, fourth means for fracturing a portion of said ionized molecules to form daughter ions as a function of fracturing energy, said third means including fifth means for generating a sequence of electric fields at predetermined times in said drift region substantially parallel to said longitudinal axis to reposition and move said ionized molecules and daughter ions toward a collector positioned at said second end of said drift region.

6. The apparatus of claim 5 wherein said fourth means for fracturing includes means for applying an electric field of a predetermined magnitude.

7. The apparatus of claim 5 wherein said fourth means for fracturing includes means for applying an electric field having a first polarity and a second polarity as a function of distance along said longitudinal axis at first times and a reversed polarity at second times.

8. Apparatus for chemically reacting selected ions of predetermined mobility comprising:

an inlet means for introducing a carrier gas and a sample gas into a reaction region, first means for generating positive and negative ions from said carrier gas and sample gas in said reaction region, second means for generating an electric field in said reaction region to move ions of a first polarity at first times and ions of a second polarity at second times toward a first end of a drift region having a second end and a longitudinal axis, third means for generating a sequence of electric fields at predetermined times in said drift region substantially parallel to said longitudinal axis to isolate and position ions of said first polarity having a predetermined mobility in said drift region at a first predetermined distance from said first end, said third means including fourth means for generating a sequence of electric fields at predetermined times in said drift region at distances less than said first predetermined distance from said first end substantially parallel to said longitudinal axis to isolate and position ions of said second polarity having a predetermined mobility at a second predetermined distance from said first end, said third means including fifth means for generating an electric field in said drift region to move said ions of first polarity and said ions of second polarity toward each other to permit said ions of first and second polarity to chemically combine.

9. The apparatus of claim 8 further including a membrane positioned transverse to said longitudinal axis and between said first and second predetermined distances in said drift region.

10. The apparatus of claim 9 wherein said membrane includes a catalyst to aid a chemical reaction.

11. The apparatus of claim 9 wherein said membrane includes means for maintaining said membrane at a predetermined temperature.

12. Apparatus for holding ions at a location comprising:

first inlet means for introducing a carrier gas and a sample gas into a reaction region, a second inlet means for introducing a drift gas into a drift region and at a pressure wherein the mean free path of the drift gas is a small fraction of the dimensions of the drift region, first means for generating ions from said carrier gas and sample gas in said reaction region, second means for generating an electric field in said reaction region to move said ions toward a first end of said drift region having a second end and a longitudinal axis, third means for generating an electric field in said drift region substantially parallel to said longitudinal axis, said electric field at first times having a first direction at said first end to accept ions from said reaction region, and a transition region at said location between said first and second ends where said electric field reverses direction with respect to said first direction to provide an ion well for holding ions.

13. The apparatus of claim 12 wherein said third means for generating an electric field in said drift region includes fourth means for increasing the magnitude of the electric field in said transition region at second times to compress said ions within a shorter distance along said longitudinal axis in said transition region.

14. A method for detecting first ions comprising the steps of introducing a carrier gas and a sample gas into a reaction region, introducing a drift gas into a drift region and at a pressure wherein the mean free path of the drift gas is a small fraction of the dimensions of the drift region, generating first ions from said carrier gas and sample gas in said reaction region; generating an electric field in said reaction region to move said first ions toward said drift region having a longitudinal axis, generating an electric field in said drift region substantially parallel to said longitudinal axis to move said first ions toward a collector at first times, generating an electric field in said drift region substantially parallel to said longitudinal axis to move said first ions away from said collector at second times, and generating an electric field in said drift region substantially parallel to said longitudinal axis to move said first ions toward said collector at third times.

15. The method of claim 14 wherein said step of generating an electric field in said reaction region includes generating an electric field in said reaction region during said first and second times to move second ions of a first polarity toward a shutter for holding said second ions, opening said shutter to release said second ions of first polarity into said drift region at the beginning of third times to join with said other ions in said drift region.

16. A method for holding ions comprising the steps of:
introducing a carrier gas and a sample gas into a reaction region,
introducing a drift gas into a drift region and at a pressure wherein the mean free path of the drift gas is a small fraction of the dimensions of the drift region,
generating ions from said carrier gas and sample gas in said reaction region,
generating an electric field in said reaction region to move said ions toward a first end of said drift region having a second end and a longitudinal axis,
generating an electric field in said drift region substantially parallel to said longitudinal axis, said electric field at first times having a first direction at said first end to accept ions from said reaction region, and a transition region between said first and second ends where said electric field reverses direction with respect to said first direction to provide an ion well for holding ions.

17. The method of claim 16 wherein said step of generating an electric field in said drift region includes increasing the magnitude of the electric field in said transition region at second times to compress said ions within a shorter distance along said longitudinal axis in said transition region.

18. A method for identification of ionized molecules having a similar mobility ($K_O$) but having dissimilar atomic mass unit (AMU) and fracturing energy levels comprising the steps of:
introducing a carrier gas and a sample gas into a reaction region,
generating ions from said carrier gas and sample gas in said reaction region, generating an electric field in said reaction region to move said ions toward a first end of a drift region having a second end and a longitudinal axis,
generating a sequence of electric fields at predetermined times in said drift region substantially parallel to said longitudinal axis to isolate and position said ionized molecules having a similar mobility in said drift region,
fracturing a portion of said ionized molecules to form daughter ions as a function of fracturing energy, and
generating a sequence of electric fields at predetermined times in said drift region substantially parallel to said longitudinal axis to reposition and move said ionized molecules and daughter ions toward a collector positioned at said second end of said drift region.

19. The method of claim 18 wherein said step of fracturing includes applying an electric field of a predetermined magnitude.

20. The method of claim 18 wherein said step of fracturing includes applying an electric field having a first polarity and a second polarity as a function of distance along said longitudinal axis at first times and a reversed polarity at second times.

21. A method for chemically reacting selected ions of predetermined mobility comprising the steps of:
introducing a carrier gas and a sample gas into a reaction region,
generating positive and negative ions from said carrier gas and sample gas in said reaction region,
generating an electric field in said reaction region to move ions of a first polarity at first times and ions of a second polarity at second times toward a first end of a drift region having a second end and a longitudinal axis,
generating a sequence of electric fields at predetermined times in said drift region substantially parallel to said longitudinal axis to isolate and position ions of said first polarity having a predetermined mobility in said drift region at a first predetermined distance from said first end, generating a sequence of electric fields at predetermined times in said drift region at distances less than said first predetermined distance from said first end substantially parallel to said longitudinal axis to isolate and position ions of said second polarity having a predetermined mobility at a second predetermined distance from said first end, and
generating an electric field in said drift region to move said ions of first polarity and said ions of second polarity toward each other to permit said ions of first and second polarity to chemically combine.

22. The method of claim 21 further includes the step of placing a membrane positioned transverse to said longitudinal axis and between said first and second predetermined distances in said drift region.

23. The method of claim 21 further includes the step of placing a catalyst to aid a chemical reaction.

24. The apparatus of claim 22 further includes the step of maintaining said membrane at a predetermined temperature.

* * * * *